United States Patent [19]

Patel

[11] 4,044,758
[45] Aug. 30, 1977

[54] CHOLANGIOGRAPHY DEVICE AND METHOD

[75] Inventor: Bhupendra C. Patel, Elgin, Ill.

[73] Assignee: The Kendall Company, Boston, Mass.

[21] Appl. No.: 649,112

[22] Filed: Jan. 14, 1976

[51] Int. Cl.² .............................................. A61B 6/00
[52] U.S. Cl. ................................. 128/2 A; 128/218 M; 128/234
[58] Field of Search ................. 128/2 A, 2 R, 218 P, 128/218 M, 218 NV, 234, 348

[56] References Cited

U.S. PATENT DOCUMENTS

| | | | |
|---|---|---|---|
| 1,860,898 | 5/1932 | Meyer | 128/218 NV |
| 2,687,728 | 8/1954 | Copen | 128/218 D |
| 2,869,543 | 1/1959 | Ratcliff et al. | 128/234 X |
| 2,939,459 | 6/1960 | Lazarte et al. | 128/218 M |
| 3,091,240 | 5/1963 | McConnaughey et al. | 128/218 NV |
| 3,115,875 | 12/1963 | Wilburn | 128/218 NV |
| 3,303,846 | 2/1967 | Ogle | 128/218 M |
| 3,399,668 | 9/1968 | Lundgren | 128/348 X |
| 3,888,239 | 6/1975 | Rubinstein | 128/2 A |
| 3,918,456 | 11/1975 | Patel | 128/348 |

*Primary Examiner*—Dalton L. Truluck
*Attorney, Agent, or Firm*—Powell L. Sprunger

[57] ABSTRACT

A device for use in cholangiography and similar procedures comprising, a syringe having a barrel defining a chamber. The syringe has a plunger having one end received in a proximal end of the syringe chamber for pumping liquid from the chamber, a floating barrier received in the chamber and defining a first compartment intermediate the barrier and a distal end of the chamber for retaining an irrigation liquid and a second compartment intermediate the barrier and the one end of the plunger for retaining a liquid contrast medium. The device has a catheter having a distal end, a proximal end, and a lumen extending through the catheter. The device has a liquid receiving receptacle having a chamber, means for selectively connecting the syringe to the catheter lumen and the receptacle chamber, and means for establishing communication between the connecting means and the second compartment when the barrier is located adjacent the distal end of the chamber.

22 Claims, 15 Drawing Figures

CHOLANGIOGRAPHY DEVICE AND METHOD

BACKGROUND OF THE INVENTION

The present invention relates to a device for use in cholangiography or similar procedures.

Cholangiography may be defined as an X-ray of the biliary duct system of a patient to determine whether gall stones are present in the system. During cholecystectomy, i.e., surgical removal of the patient's gall bladder, the surgeon usually attempts to ascertain whether gall stones are present in the duct system, particularly the common bile duct, and thus must be removed. However, choledochotomy, i.e., the surgical incision of the common bile duct, should be avoided if stones are not present in the common duct, since this procedure, just as overlooked stones, may be a source of post-cholecystectomy morbidity. Thus, cholangiography should be performed before surgical intervention into the common duct to eliminate an unnecessary choledochotomy.

In the past, operative cholangiography has been most simply performed in the following manner. A syringe containing a saline solution is attached to a proximal end of a catheter, an incision is made in the patient's cystic duct, which extends between the gall bladder and the common duct, and a distal end of the saline filled catheter is inserted through the incision and is positioned adjacent the juncture of the cystic duct and common duct. Next, the syringe plunger is depressed in order to irrigate the duct system with the saline solution, thus flushing the common duct to remove bile fluid, debris, and air, and to provide an indication that the common duct is not blocked. Normally, a relatively small quantity of saline solution is required to perform the irrigation procedure.

The irrigation syringe is then removed from the catheter, and another syringe containing a liquid contrast medium is attached to the proximal end of the catheter, after which the contrast medium is ejected from the catheter into the duct system. At this time, a cholangiogram, i.e., an X-ray, is obtained of the duct system, on which the stones appear as dark round shadows since they are less dense to the X-rays than the contrast medium. Additional cholangiograms are normally obtained while using increased quantities of the contrast medium.

Air bubbles, if present in the duct system during cholangiography, also appear as dark round shadows similar to stones on the cholangiograms. Hence, air must be prevented from entering the duct system during cholangiography, since the bubbles are likely to be interpreted as stones on the cholangiogram. In the past, the cholangiography devices offered an opportunity for air to enter the system when the syringes are changed. Thus, air bubbles may be injected into the duct system by the prior devices, and may result in an unnecessary and undesirable choledochotomy attendant with loss of confidence in cholangiography by the surgeon when no stones are found during the choledochotomy.

SUMMARY OF THE INVENTION

A principal feature of the present invention is the provision of a device of simplified construction for performing cholangiography and similar procedures in an improved manner.

The device of the present invention comprises a syringe having a barrel defining a chamber, a plunger having one end received in a proximal end of the syringe chamber for pumping liquid from the chamber, and a floating barrier received in the chamber. The barrier defines a first compartment intermediate the barrier and a distal end of the chamber for retaining an irrigation liquid and a second compartment intermediate the barrier and the one end of the plunger for retaining a liquid contrast medium. The device has a catheter having a distal end, a proximal end, and a lumen extending through the catheter. The device has a liquid receiving receptacle having a chamber, means for selectively connecting the syringe to the catheter lumen and the receptacle chamber, and means for establishing communication between the connecting means and the second compartment when the barrier is located adjacent the distal end of the chamber.

A feature of the present invention is that an initial portion of the irrigation liquid may be pumped through the catheter lumen.

Another feature of the present invention is that a remaining portion of the irrigation liquid may be pumped into the receptable chamber until the barrier is located adjacent the distal end of the chamber to establish communication with the second compartment.

A further feature of the present invention is that the liquid contrast medium may then be pumped through the catheter lumen.

Still another feature of the invention is that the irrigation liquid and contrast medium may be pumped through the catheter lumen without introducing air into the device.

Thus, a feature of the present invention is that the device may be used to perform cholangiography without introducing air bubbles into the biliary duct system of the patient, and the device prevents an erroneous indication of a gall stone on a cholangiogram during cholangiography.

A feature of the present invention is that in an embodiment the device has valve means for separately connecting the syringe needle to the catheter lumen and the receptacle chamber.

Another feature of the present invention is that in an embodiment the device has a flexible bulb for directing liquid passage from the syringe needle to the catheter lumen and the receptacle chamber.

Yet another feature of the invention is the provision of a needleless syringe for retaining liquids in separate compartments of the syringe.

Still another feature of the invention is the provision of a method for filling the syringe chamber.

Further features will become more fully apparent in the following description of the embodiments of this invention and from the appended claims.

DESCRIPTION OF THE PREFERRED EMBODIMENTS

Figure 1:
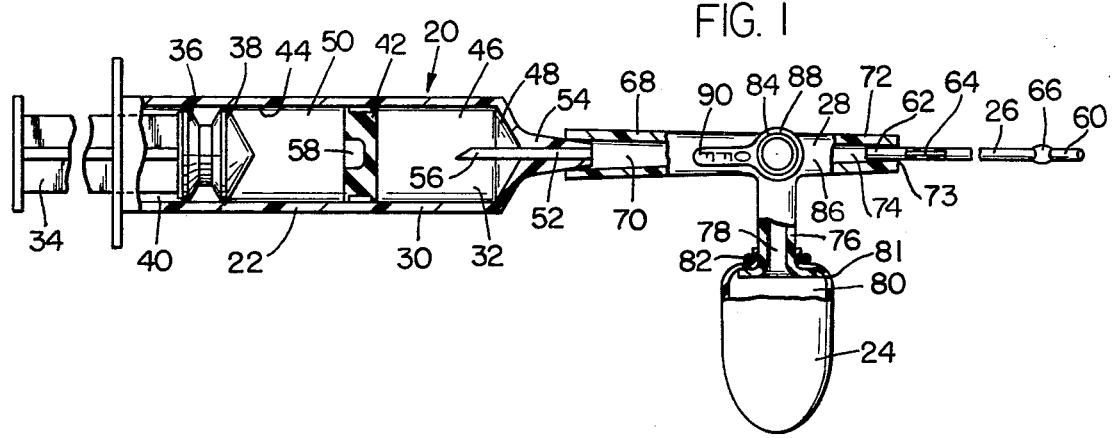
FIG. 1 is a fragmentary elevational view, taken partly in section, of a cholangiography device of the present invention.

Referring now to FIG. 1, there is shown a device generally designated 20 for performing cholangiography and similar procedures. The device 20 has a syringe 22, a receptacle 24, a catheter 26, and a hollow connector 28 connecting the syringe 22, the receptacle 24, and the catheter 26.

Figure 5:
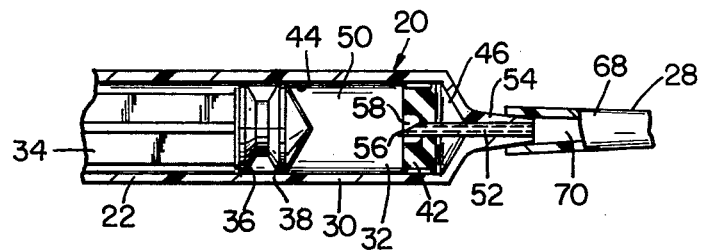
FIG. 5 is a fragmentary sectional view showing a syringe needle in the device of FIG. 1 as puncturing a barrier in the syringe.

The syringe 22 has a barrel 30 defining a chamber 32, and a plunger 34 having one end 36 containing a flexible plug 38 received in a proximal end 40 of the chamber 32. The syringe 22 has a floating barrier 42 of flexible material, such as rubber, received in the chamber 32, and sealingly engaging against an inner surface 44 of the syringe barrel 30. The barrier 42 separates the syringe chamber 32 into a first compartment 46 located intermediate the barrier 42 and a distal end 48 of the chamber 32 for retaining an irrigation liquid, such as a saline solution, and a second compartment 50 located intermediate the barrier 42 and the one end 36 of the plunger 34 for retaining a liquid contrast medium of known type which is opaque to X-rays. Preferably, the syringe is prefilled prior to the time of use. The syringe 22 also has a hollow needle 52 retained in a tip 54 of the syringe. The needle 52 has a sharp inner end portion 56 projecting into the syringe chamber 32, and extending a sufficient distance into the syringe chamber 32 to puncture the barrier 42 when the barrier is located adjacent the distal end 48 of the chamber 32, as shown in FIG. 5. As illustrated in FIGS. 1 and 5, the barrier 42 has a recess 58 facing the second compartment 50 to receive the inner end portion 56 of the needle 52.

Referring to FIG. 1, the catheter has a distal end 60, a proximal end 62, and a lumen 64 extending between the distal and proximal ends 60 and 62 of the catheter 26. The catheter 26 may also have an outer bead 66 spaced slightly from the distal end 60 of the catheter 26 for a purpose which will be described below.

The connector 28 has a first end portion 68 defining a first passageway 70 which receives the syringe tip 54 and communicates with a lumen in the needle 52. The connector 28 also has a second end portion 72 defining a second passageway 74 and having an opening 73 to receive the proximal end 62 of the catheter 26, such that the second passageway 74 communicates with the lumen 64 of the catheter 26. The connector 28 also has a third end portion 76 defining a third passageway 78. The receptacle 24 has a liquid receiving chamber 80, and the receptacle 24 is attached to an outer end of the third connector portion 76 over a flange 81 by suitable means, such as a band 82, such that the third passageway 78 communicates with the receptacle chamber 80.

Figure 3:
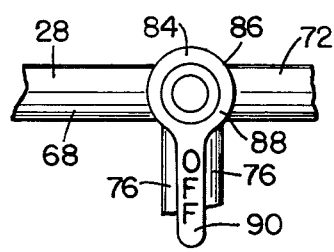
FIGS. 3 and 3A are fragmentary elevational and sectional views, respectively, showing a valve in the device of FIG. 1 at a first rotational position.
Figure 3A:
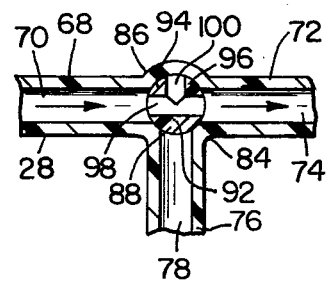
Figure 4:
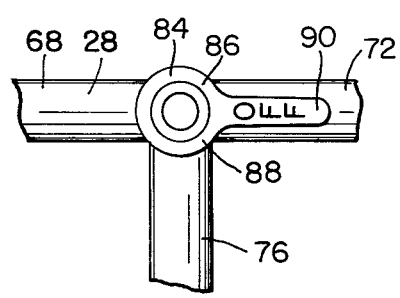
FIGS. 4 and 4A are fragmentary elevational and sectional views, respectively, showing the valve in the device of FIG. 1 at a second rotational position.

As illustrated in FIGS. 1, 3, 3A, 4, and 4A, the connector 28 also has a valve 84, with the connector 28 defining a housing 86 for the valve, and with the valve 84 having a valve member 88 rotatably received in the valve housing 86. As illustrated in FIGS. 1, 3, and 4, the valve member 88 has a handle 90 to facilitate movement of the valve member 88 in the housing 86 between rotational positions of the valve member.

Figure 4A:
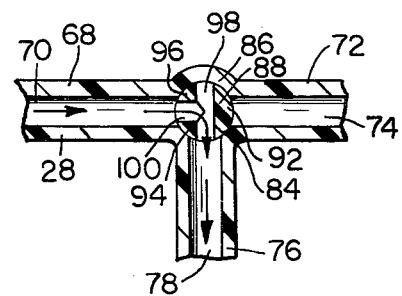

Referring to FIG. 3A, the valve member 88 has first, second, and third wall sections 92, 94, and 96, respectively, defining a first channel 98 extending through the valve member 88, and a second channel 100 extending between the first channel 98 and the outside of the valve member 88. With reference to FIGS. 3 and 3A, when the valve member 88 is positioned at a first rotational position with the handle 90 aligned with the third connector portion 76, the first channel 98 communicates between the first passageway 70 and the second passageway 74 of the connector 28. Thus, in this configuration, the valve 84 permits passage of liquid from the syringe needle through the first channel 98 of the valve member 88 to the catheter lumen, while the first wall section 92 of the valve member 88 prevents passage of liquid into the third passageway 78 of the connector 28. Referring to FIGS. 4 and 4A, when the valve member is moved to a second rotational position, with the handle 90 aligned with the second connector portion 72, the first and second channels 98 and 100 are respectively aligned with the third and first passageways 78 and 70 of the connector 28, and the valve 84 establishes communication between the first and third passageways 70 and 78 of the connector 28. Thus, in this configuration of the valve 84, the valve member 88 permits passage of liquid from the first connector passageway 70 through the second channel 100 of the valve member 8, a portion of the first channel 98 of the valve member 88, the third connector passageway 78 and into the receptacle chamber 80, while the first wall section 92 of the valve member 88 prevents passage of liquid into the second connector passageway 74 and the catheter lumen 64. Finally, with reference to FIG. 1, at a third rotational position of the valve member 88, it will be apparent that the first wall section 92 of the valve member 88 blocks the first passageway 70 of the connector, since the second channel 100 of the valve member 88 is aligned with the third connector passageway 74.

Figure 2:
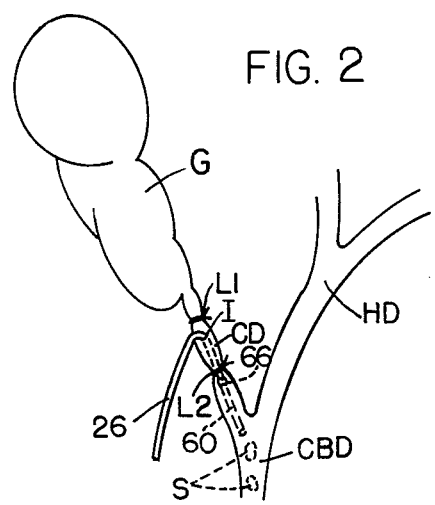
FIG. 2 is a diagrammatic view showing a catheter of the device of FIG. 1 in position for performing cholangiography.

The use of the device 20 of the present invention for performing cholangiography is described as follows. Referring to FIGS. 1, 3, and 3A., the handle 90 is utilized to position the valve member 88 at its first rotational position, such that communication is established through the valve member 88 between the syringe needle 52 and the catheter lumen 64. Next, the syringe plunger 34 may be pushed slightly into the syringe chamber 32 in order to eject a small quantity of the irrigation liquid through the needle 52, the connector 28 and valve 84, and through the lumen 64 of the catheter 26, thus expelling any air from the device. Next, with reference to FIG. 2, the surgeon normally places a ligature L1 around the cystic duct CD adjacent the gall bladder G, and makes an incision I in the cystic duct CD. The surgeon then inserts the distal end 60 of the catheter 26 through the incision I abd the cystic duct CD until the distal end 60 of the catheter 26 is located adjacent the juncture of the cystic duct CD, the hepatic duct HD, and the common bile duct CBD, after which a ligature L2 may be tied around the cystic duct CD proximal the catheter bead 66 in order to retain the catheter 26 at its desired position in the cystic duct CD.

The surgeon then pushes the plunger 34 into the syringe chamber 32 to eject a quantity of the irrigation liquid through the syringe needle 52, the connector 28, and the catheter 26 into the biliary duct system including the common bile duct CBD, thus flushing the duct system and determining whether the common duct CBD permits passage of liquid and is not blocked. Normally, the flushing procedure requires a relatively small amount of irrigation liquid.

When the irrigation procedure has been completed, the surgeon may utilize the handle 90 of the valve member 88 to position the valve member 88 at its second rotational position, as illustrated in FIGS. 4 and 4A. The syringe plunger 34 is then depressed a sufficient distance into the chamber 32 to eject a remaining portion of the irrigation liquid through the needle 52, the valve member 88, and into the receptacle chamber 80 for collection therein. As the surgeon depresses the plunger 34 into the syringe chamber and the first compartment 46 empties, the inner end portion 56 of the needle 52 punctures the barrier 42, as shown in FIG. 5, such that communication is established between the second compartment 50 of the syringe chamber 32 and the needle 52. At this time, the surgeon uses the handle 90 of the valve member 88 to again locate the valve member 88 at its first rotational position, as illustrated in FIGS. 3 and 3A. In this configuration, communication is established between the syringe needle 52 and the catheter lumen 64, such that the liquid contrast medium in the second compartment 50 of the syringe 22 may be ejected through the syringe needle 52, the connector 28, and the catheter lumen 64 into the duct system of the patient. When a sufficient quantity of the liquid contrast medium has been pumped into the duct system, an X-ray of the duct system may be taken in order to obtain a cholangiogram and determine whether any stones S are present which should be removed. The syringe plunger 34 may be pushed further into the syringe chamber 32 to eject additional amounts of the contrast medium and obtain further cholangiograms of the duct system, if desired.

Thus, according to the present invention, the device 20 permits the surgeon to pump the irrigation liquid into the duct system, to discard the remaining portion of the irrigation liquid, and to pump the liquid contrast medium into the duct system, in order to flush the duct system and obtain cholangiograms. The device of the present invention permits cholangiography to be performed in a simplified manner, and the irrigation liquid and contrast medium may be pumped into the duct system without introducing air into the system. Accordingly, the device 20 prevents passage of air bubbles into the duct system, and thus prevents a possible false indication of a stone in the duct system on the cholangiograms, which otherwise might result in an unnecessary and undesired incision of the common duct or system.

Figure 6:
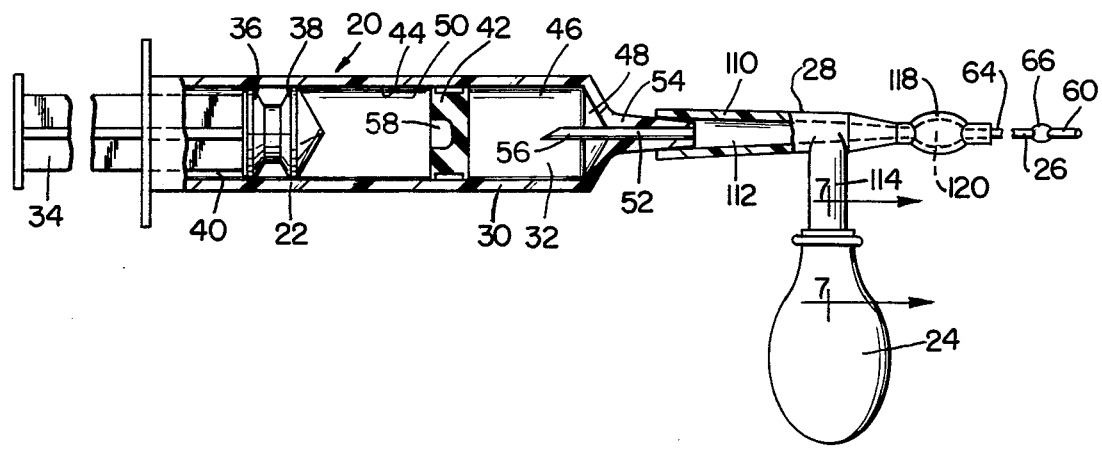
FIG. 6 is a fragmentary elevational view, taken partly in section, showing another embodiment of the device of the present invention.
Figure 7:
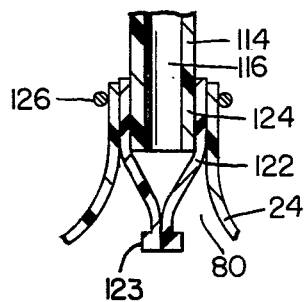
FIG. 7 is a fragmentary sectional view taken substantially as indicated along the line 7—7 of FIG. 6.

Another embodiment of the present invention is illustrated in FIGS. 6 and 7, in which like reference numerals designate like parts. In this embodiment, the connector 28 has a first portion 110 defining a first passageway 112, and a second portion 114 defining a second passageway 116 communicating with the first passageway 112. The device also has a flexible hollow bulb or tubular section 118 defining a channel 120 communicating between the first connector passageway 112 and the lumen of the catheter 26. The bulb 118 may be constructed as an extension of the connector 28 or the catheter 26, or separately, as desired, and may be made of any suitable elastic material, such as rubber. As shown in FIG. 7, the device 20 has a flap valve 122 secured to an outer end 124 of the second connector portion 114. The valve 122 may be made of any suitable material, such as rubber, and has a thick end portion 123 which serves as a reinforcement to prevent premature opening of the valve 122. Also, as shown in FIGS. 6 and 7, the receptacle 24 may be connected to the outer end 124 of the second connector portion 114 by any suitable means, such as by a band 126.

In use of the device, the irrigation liquid may be pumped from the first compartment 46 of the syringe by pushing the plunger 34 into the syringe chamber 32 as previously described, and the irrigation liquid is thus pumped through the syringe needle 56, the first connector passageway 112, the channel 120 of the bulb 118, and the catheter lumen into the duct system. During this time, the flap valve 122 prevents passage of liquid from the second connector passageway 116 into the receptacle chamber 80, since the flap valve 122 opens only above a predetermined pressure which is substantially greater than that normally required to pump the liquid through the bulb 118 and the catheter lumen into the duct system.

When the flushing procedure has been completed, the surgeon may press the flexible bulb 118 to close the bulb channel 120. In this configuration, when the syringe plunger is further pushed into the syringe chamber 32, the pressure generated by the syringe becomes sufficiently large to open the flap valve 122, and the remaining portion of the irrigation liquid may be discarded through the syringe needle 52, the connector 28, and the flap valve 122 which opens into the receptacle chamber 80. Thus, the remaining portion of the irrigation liquid may be pumped into the receptacle chamber until the inner end portion 56 of the syringe needle 52 punctures the syringe barrier 42, after which communication is established between the needle 52 and the second compartment 50 of the syringe. At this time, the flexible bulb 118 may be released in order to open the bulb channel 120 and permit closure of the valve 122. As the surgeon further pushes the syringe plunger 34 into the syringe chamber 32, the liquid contrast medium is pumped through the syringe needle 52, the connector 28, the bulb 118, and the catheter 26 into the duct system of the patient, while the closed valve 122 again prevents passage of liquid into the receptacle chamber 80. According to the present invention, the device of FIGS. 6 and 7 permits the irrigation liquid and contrast medium to be pumped into the duct system of the patient without introducing air bubbles into the device or the duct system, thus preventing a possible false indication of a stone on the cholangiograms.

Figure 8:
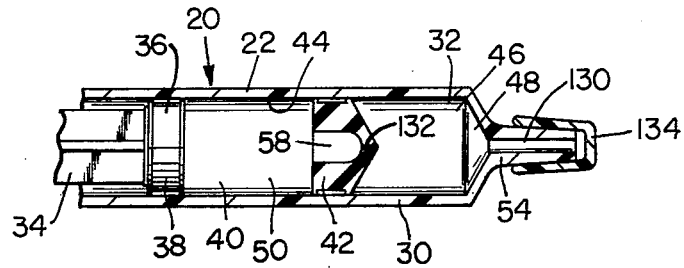
FIG. 8 is a fragmentary sectional view of another embodiment of the present invention.

Another embodiment of the present invention is illustrated in FIG. 8, in which like reference numerals designate like parts. In this embodiment, the syringe 22 has an opening 130 extending through the tip 54 of the syringe 22, but does not have a needle. The barrier 42 has normally closed opening means 132, such as a slit, extending through the barrier 42 between the recess 58 and the first compartment 46 of the syringe. In a preferred form, the compartments 46 and 50 of the syringe are prefilled before the time of use, and the syringe 22 may have a cap 134 releasably attached to the syringe tip 54 to prevent leakage of the solution in the first compartment 46 out of the syringe.

In use, the cap 134 may be removed from the syringe tip 54, and the syringe tip 54 may be attached to a connector 28 in the devices previously described in connection with FIGS. 1 or 6. The syringe of FIG. 8 may then be utilized in a manner as previously described to flush the biliary duct system of the patient with the irrigation liquid. After the flushing procedure has been completed, the remaining portion of the solution in the first compartment 46 may be discarded into the receptacle, at which time the barrier 42 of the syringe 22 will be located adjacent the distal end 48 of the syringe chamber 32 with the opening means 132 of the barrier 42 being aligned with the opening 130 in the syringe tip 54. When it is desired to obtain a cholangiogram, the syringe plunger 34 may be depressed an additional amount into the syringe chamber 32, such that the pressure generated in the second compartment 50 of the syringe 22 causes the opening means 132 to open from its initially closed configuration, thus permitting passage of the liquid contrast medium from the second compartment 50 through the opening means 132 to the syringe tip 54 and then through the catheter into the duct system. When the syringe plunger 34 is released between separate cholangiograms, the opening means 132 of the barrier 42 closes to prevent passage of contrast medium from the second compartment 50 through the barrier 42.

Figure 9:
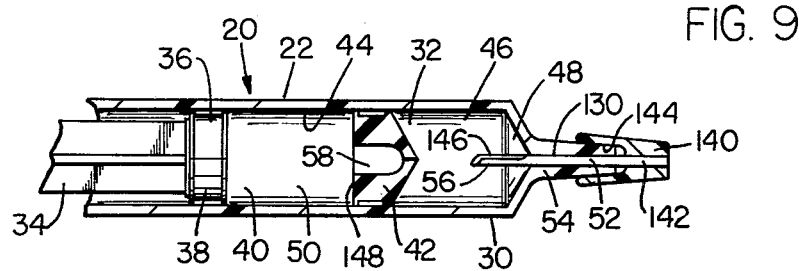
FIGS. 9-13 are fragmentary sectional views illustrating a syringe being filled according to a method of the present invention.

A device 20 which permits filling of the syringe 22 at the time of use according to a method of the present invention is described in connection with FIGS. 9–13, in which like reference numerals designate like parts. As shown in FIG. 9, the syringe 22 includes a hub 140 which retains an outer end 142 of the needle 52. The hub 142 has a recess 144 to receive the syringe tip 54, such that the hub 140 may be releasably attached to the syringe tip 54 with the needle 52 received through the opening 130 in the syringe tip 54, and with the inner end portion 56 of the needle 52 projecting into the syringe chamber 32. In a preferred form, the inner end portion 56 of the needle 52 has an elongated slot 146 for a purpose which will be described below.

Figure 10:
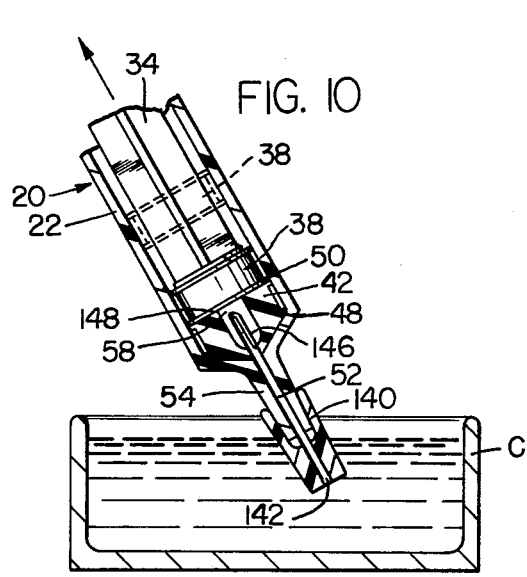
Figure 11:
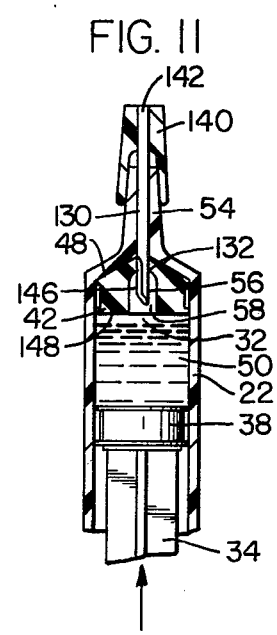

When it is desired to fill the compartments of the syringe immediately prior to use, the syringe plunger 34 is pushed into the chamber its full range to move the barrier 42 against the distal end 48 of the syringe chamber 32, such that the needle 52 punctures the barrier 42. With reference to FIG. 10, in this configuration the inner end portion 56 of the needle 52 is received in the barrier recess 58, and the plunger plug 38 is located at the back surface 148 of the barrier 42. Next, the outer end of the hub 140 may be dipped into a supply of liquid contrast medium retained in a container C in order to establish communication between the second compartment and the supply through the needle. The plunger 34 is then partially withdrawn from the syringe chamber in order to aspirate the contrast medium through the needle 52 into the barrier recess 58 and the second compartment 50 of the syringe chamber which is enlarged as the plunger plug 38 moves away from the barrier 42 (shown in dotted lines in FIG. 10), while the barrier 42 remains in place at the distal end 48 of the syringe chamber. When a sufficient quantity of liquid contrast medium has been obtained in the second compartment 50 of the syringe, the syringe may be inverted into the configuration shown in FIG. 11 with the syringe tip 54 directed in an upright position, such that any air contained in the second compartment 50 of the syringe will move to the upper part of the second compartment and into the recess 58 of the barrier 42. As shown, the needle slot 146 communicates with the upper end of the barrier recess 58 and the air may be expelled by pushing the plunger 34 slightly into the syringe chamber, with the air passing through the slot 146 and the needle 52 out of the syringe. At this time, the hub 140 and attached needle 52 may be removed from the syringe tip 54, and the barrier opening means 132, formed by the needle puncture through the carrier 42, closes to seal the second compartment 50 after all air has been removed.

Figure 12:
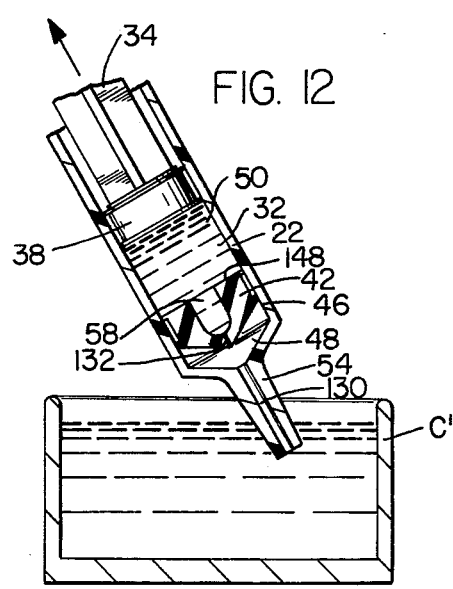
Figure 13:
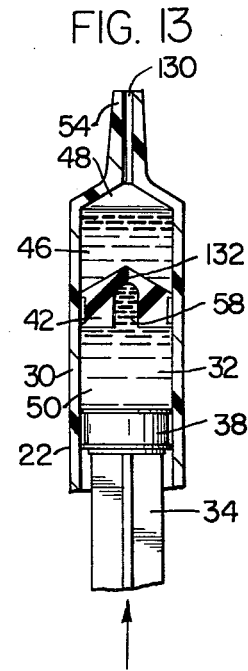

With reference to FIG. 12, the syringe tip 54 may be placed in a source of irrigation solution retained in the container C', and the syringe plunger 34 may be withdrawn toward the proximal end of the syringe chamber in order to aspirate the irrigation solution through the opening 130 of the syringe tip 54 into the first compartment 46 of the syringe which is enlarged as the barrier 42 moves away from the distal end 48 of the chamber. During this time, the closed puncture or opening means 132 of the barrier 42 prevents passage of the irrigation solution from the first compartment 46 into the second compartment 50 of the syringe chamber. When a sufficient quantity of irrigation solution has been obtained in the first compartment 46 of the syringe, the syringe may be placed in an inverted configuration with the syringe tip 54 in an upright position, as illustrated in FIG. 13. Accordingly, any air which may be contained in the first compartment 46 will move toward the upper end of the first compartment 46, and the air may be expelled through the syringe tip 54 by pushing the plunger 34 slightly into the syringe chamber 32. At this time, the filled syringe 22 is ready for use with the liquid contrast medium being located in the second compartment 50, with the irrigation solution being located in the first compartment 46, and with all air being removed from the first and second compartment 46 and 50, respectively.

In a preferred form of use, the syringe tip 54 of the filled syringe may be directly attached to a connector 28 described in connection with FIGS. 1 or 6, and the syringe operates during cholangiography in a manner as previously described in connection with the syringe of FIG. 8. Thus, the needle puncture or opening means 132 which extends through the barrier 42 between the recess 58 and the first compartment 46 serves to establish communication between the second compartment 50 and the syringe tip 54 when the barrier 42 is located adjacent the distal end 48 of the syringe chamber 32 and when the syringe plunger 34 is pushed a sufficient amount to generate pressure in the second compartment and open the opening means 132. Alternatively, if desired, the hub 140 and retained needle 52 may be repositioned on the syringe tip 54, and one of the connectors 28 described in connection with FIGS. 1 or 6 may be attached to the outer end of the hub 140. In this configuration, the inner end portion 56 of the needle 52 again punctures the barrier 42 when the barrier is located adjacent the distal end 48 of the syringe chamber 32 in order to establish communication with the second compartment 50 of the syringe chamber.

The foregoing detailed description is given for clearness of understanding only, and no unnecessary limitations should be understood therefrom, as modifications will be obvious to those skilled in the art.

I claim:

1. A device for use in cholangiography and similar procedures, comprising:
   a syringe having a barrel defining a chamber, a plunger having one end received in a proximal end of the syringe chamber for pumping liquid from the chamber, a floating barrier received in the chamber and defining a first compartment intermediate the barrier and a distal end of the chamber for retaining an irrigation liquid and a second compartment intermediate the barrier and said one end of the plunger for retaining a liquid contrast medium;

a catheter having a distal end, a proximal end, and a lumen extending through the catheter;

a liquid receiving receptacle having a chamber;

means for selectively connecting the syringe to the catheter lumen and the receptacle chamber; and means for establishing communication between the connecting means and said second compartment when said barrier is located adjacent the distal end of the chamber, whereby an initial portion of the irrigation liquid may be pumped through the catheter, a remaining portion of the irrigation liquid may be pumped into the receptacle chamber until the barrier is located adjacent the distal end of the syringe chamber to establish communication with the second compartment, and the liquid contrast medium may be pumped through the catheter lumen without introducing air into the device.

2. The device of claim 1 wherein the connecting means comprises valve means for separately connecting said syringe to the receptacle chamber and the catheter lumen.

3. The device of claim 2 wherein the connecting means includes a connector having a first passageway communicating with said syringe, a second passageway communicating with a proximal end portion of the catheter lumen, and a third passageway communicating with the receptacle, and in which the valve means connects said first and second passageways to establish communication between the syringe and the catheter lumen, and separately connects the first and third passageways to establish communication between the syringe and the receptacle chamber.

4. The device of claim 3 wherein the valve means comprises a valve housing and a valve member rotatably mounted in said housing, said valve member having a first channel extending through the valve member and communicating between said first and second passageways at a first rotational position of the valve member, with said first channel communicating with the third passageway at a second rotational position of the valve member, said valve member having a second channel communicating between the first channel and the first passageway at said second rotational position of the valve member.

5. The device of claim 4 wherein said first channel communicates with said third passageway and the second channel communicates with said second passageway at a third rotational position of the valve member.

6. The device of claim 1 wherein the connecting means comprises a connector having a first hollow connecting portion attached to the syringe, a second hollow connecting portion attached to the proximal end of said catheter, and a third hollow connecting portion communicating with said first and second connecting portions, said receptacle being attached to said third connecting portion.

7. The device of claim 1 wherein the connecting means comprises a hollow connector attached to the syringe and said receptacle, and means connected between the connector and the catheter for selectively preventing and permitting communication between the connector and the catheter.

8. The device of claim 7 wherein the preventing and permitting means comprises an extension of said connector.

9. The device of claim 7 wherein the preventing and permitting means comprises an extension of said catheter.

10. The device of claim 7 including valve means effectively connected between said connector and receptacle chamber for preventing passage of liquid from said syringe into the receptacle chamber below a predetermined pressure in the connector and permitting passage of liquid from the syringe into the receptacle chamber above a predetermined pressure.

11. The device of claim 7 wherein the preventing and permitting means comprises a flexible tubular member, said tubular member being closed to prevent passage of liquid into the catheter and being released to permit passage of liquid into the catheter.

12. The device of claim 11 wherein said tubular member comprises a flexible bulb.

13. The device of claim 1 wherein the connecting means comprises a connector having a first portion defining a first passageway, and a second portion defining a second passageway communicating with said first passageway, a hollow flexible bulb communicating between the first passageway and the catheter lumen, said bulb being closed to prevent passage of liquid from the first passageway into the catheter lumen and being released to permit passage of liquid from said first passageway into the catheter lumen, and valve means associated with said second passageway, said receptacle being attached to the second connector portion with the valve means being effectively positioned between the first passageway and the receptacle chamber, said valve means closing when said bulb is released to prevent passage of liquid from the first passageway into the receptacle chamber, and said valve means opening when said bulb is closed and the syringe plunger is pushed into the syringe chamber to permit passage of liquid from the first passageway through the valve means into the receptacle chamber for collection therein.

14. The device of claim 13 wherein said valve means comprises a flap valve.

15. The device of claim 1 wherein the catheter includes an outer bead spaced slightly from the distal end of the catheter.

16. The device of claim 1 wherein the establishing means comprises, a hollow needle retained adjacent the distal end of said chamber, said needle initially communicating with said first compartment and projecting a sufficient distance into the chamber to puncture said barrier and communicate with said second compartment when said barrier is located adjacent the distal end of said chamber.

17. The device of claim 16 wherein said needle includes a slot communicating with said second compartment at a back surface of the barrier when the barrier is located adjacent the distal end of the chamber.

18. The device of claim 16 including means for releasably attaching said needle to the syringe.

19. The device of claim 1 wherein the establishing means comprises normally closed opening means extending through the barrier between said first and second compartments, said opening means opening responsive to pressure generated in the second compartment by said plunger with the barrier located adjacent the distal end of the chamber to establish communication with the second compartment.

20. For a syringe of the type having a barrel defining a chamber, a plunger having one end received in a proximal end of the chamber, a floating barrier received in the chamber and defining a first compartment intermediate the barrier and a distal end of the chamber for retaining a first liquid and a second compartment intermediate the barrier and said one end of the plunger for retaining a second liquid, the distal end of the chamber having a passageway therethrough, and a hollow needle positioned in the passageway and projecting a sufficient distance into the chamber to puncture the barrier when the barrier is located adjacent the distal end of the chamber, a method of filling the chamber comprising the steps of:
  establishing communication between the needle and the second compartment by puncturing the barrier with the needle;
  filling the second compartment with the second liquid through the needle by withdrawing the plunger proximally in the chamber from a location adjacent the barrier and drawing the second liquid into the second compartment;
  expelling air from the second compartment through an elongated slot of the needle located in a proximal recess of the barrier by pressing the plunger into the chamber;
  removing the needle from the syringe; and
  filling the first compartment with the first liquid by withdrawing the plunger proximally in the chamber and drawing the first liquid through the passageway and into the first compartment.

21. The method of claim 20 wherein the expelling step includes the step of positioning the barrel to locate the air in an upper end of the second compartment adjacent the barrier.

22. The method of claim 20 including the step after said second filling step of expelling air from the first compartment by positioning the barrel to locate the air in an upper end of the first compartment adjacent the distal end of the chamber and pushing the plunger sufficiently into the chamber to pump the air out of the first compartment.

* * * * *